(12) United States Patent
Gleave et al.

(10) Patent No.: US 7,285,541 B2
(45) Date of Patent: Oct. 23, 2007

(54) TREATMENT OF MELANOMA BY REDUCTION IN CLUSTERIN LEVELS

(75) Inventors: Martin Gleave, Vancouver (CA); Burkhard Jansen, Vancouver (CA)

(73) Assignee: The University of British Columbia, Vancouver (CA)

( * ) Notice: Subject to any disclaimer, the term of this patent is extended or adjusted under 35 U.S.C. 154(b) by 387 days.

(21) Appl. No.: 10/646,391

(22) Filed: Aug. 21, 2003

(65) Prior Publication Data

US 2004/0082534 A1 Apr. 29, 2004

Related U.S. Application Data

(60) Provisional application No. 60/405,193, filed on Aug. 21, 2002, provisional application No. 60/408,152, filed on Sep. 3, 2002, provisional application No. 60/319,748, filed on Dec. 2, 2002, provisional application No. 60/472,387, filed on May 20, 2003.

(51) Int. Cl.
*A61K 48/00* (2006.01)
*C07H 21/02* (2006.01)
*C07H 21/04* (2006.01)

(52) U.S. Cl. .............. 514/44; 536/23.1; 536/24.5

(58) Field of Classification Search .............. 435/6, 435/325, 375; 536/23.1, 24.5, 24.3, 24.31, 536/24.33; 514/44
See application file for complete search history.

(56) References Cited

U.S. PATENT DOCUMENTS

| | | | |
|---|---|---|---|
| 5,646,042 A | 7/1997 | Stinchcomb et al. | |
| 5,789,389 A | 8/1998 | Tarasewicz et al. | |
| 5,801,154 A * | 9/1998 | Baracchini et al. | 514/44 |
| 5,929,040 A | 7/1999 | Werther et al. | |
| 5,998,148 A | 12/1999 | Bennett et al. | |
| 6,111,094 A * | 8/2000 | Bennett et al. | 536/24.5 |
| 6,172,216 B1 | 1/2001 | Bennett et al. | |
| 6,335,194 B1 | 1/2002 | Bennett et al. | |
| 6,383,808 B1 | 5/2002 | Monia et al. | |
| 2002/0128220 A1* | 9/2002 | Gleave | 514/44 |
| 2003/0158130 A1 | 8/2003 | Gleave et al. | |
| 2004/0053874 A1* | 3/2004 | Monia et al. | 514/44 |
| 2004/0220131 A1* | 11/2004 | Jackson et al. | 514/44 |

FOREIGN PATENT DOCUMENTS

| | | | | |
|---|---|---|---|---|
| WO | WO 99/51259 | * | 10/1999 | 424/85.1 |
| WO | WO 00/34469 | | 6/2000 | |
| WO | WO 00/49937 | * | 8/2000 | 514/44 |
| WO | WO 01/46455 A2 | | 6/2001 | |
| WO | WO 02/22635 A1 | | 3/2002 | |
| WO | WO 03/062421 A1 | | 7/2003 | |
| WO | WO 03/072591 A1 | | 9/2003 | |
| WO | WO 2004/018675 A1 | | 3/2004 | |
| WO | WO 2004/018676 A2 | | 3/2004 | |

OTHER PUBLICATIONS

Branch, A good antisense molecule is hard to find, TIBS, Feb. 1998, pp. 45-50.*
Green et al., Antisense Oligonucleotides: An Evolving Technology for the Modulation of Gene Expression in Human Disease, J Am Coll Surg, Jul. 2000, vol. 191, No. 1, pp. 93-105.*
Jen et al., Suppression of Gene Expression by Targeted Disruption of Messenger RNA: Available Options and Current Strategies, Stem Cells, 2000, 18:307-319.*
Crooke, Antisense Research and Application, Chapter 1, Springer-Verlag, New York, 1998.*
Aoki et al., RNA Interference May be More Potent Than Antisense RNA in Human Cancer Cell Lines, 2003, Clinical and Experimental Pharmacology and Physiology, 30, pp. 96-102.*
Saijo et al., Pharmokinetics, Tissue Distribution, and Stability of Anitisense Oligodeoxynucleotide Phosphorothioate ISIS 3466 in Mice, 1994, Oncology Research, vol. 6, No. 6, pp. 243-249.*
Gleave et al., Targeting anti-apoptotic genes upregulated by androgen withdrawal using antisense oligonucleotides to enhance androgen- and chemo-sensitivity in prostate cancer, Investigational New Drugs, 2002, pp. 145-158, vol. 20.
Gleave et al., Use of Antisense Oligonucleotides Targeting the Antiapoptotic Gene, Clusterin/Testosterone-Repressed Prostate Message 2, To Enhance Androgen Sensitivity and Chemosensitivity in Prostate Cancer, Urology, 2001, pp. 39-49, vol. 58, XP-002262320.
Gleave et al., Antisense therapy: Current status in prostate cancer and other malignancies, Cancer and Metastasis Reviews, 2002, pp. 79-92, vol. 21.
Gleave et al., Antisense Targets to Enhance Hormone and Cytotoxic Therapies in Advanced Prostate Cancer, Current Drug Targets, 2003, pp. 209-221, vol. 4, XP-009021409.
Jones et al., Molecules in focus: Clusterin, The International Journal of Biochemistry & Cell Biology, 2002, pp. 427-431, vol. 34.
Miyake et al., Antisense TRPM-2 Oligodeoxynucleotides Chemosensitize Human Androgen-independent PC-3 Prostate Cancer Cells Both in Vitro and in Vivo, Clinical Cancer Research, 2000, pp. 1655-1663, vol. 6, XP-000960694.

(Continued)

*Primary Examiner*—Jon E. Angell
*Assistant Examiner*—Amy H. Bowman
(74) *Attorney, Agent, or Firm*—Marina Larson & Associates, LLC (57) ABSTRACT

Treatment of melanoma is achieved through reduction in the effective amount of clusterin in melanoma cells of in a mammalian subject, preferably a human. A therapeutic agent effective to reduce the effective amount of clusterin in the melanoma cells is administered to the subject. The therapeutic agent may be, for example, an antisense ODN or small inhibitory RNA (siRNA) compound targeted to clusterin. bcl-xL in a subject or cell line can also be regulated by administering to the subject or cell line an agent effective to modulate the amount of clusterin expression. In particular, in clusterin expressing cells, the expression of bcl-xL is down-regulated when the effective amount of clusterin is reduced. Such inhibition is significant because bcl-xL is known to act as an inhibitor of apoptosis.

12 Claims, 2 Drawing Sheets

OTHER PUBLICATIONS

Miyake et al., Testosterone-repressed Prostate Message-2 Is an Antiapoptotic Gene Involved in Progression to Androgen Independence in Prostate Cancer, Cancer Research, 2000, pp. 170-176, vol. 60, XP-002907064.

Miyake et al., Synergistic Chemsensitization and Inhibition of Tumor Growth and Metastasis by the Antisense Oligodeoxynucleotide Targeting Clusterin Gene in a Human Bladder Cancer Model, Clinical Cancer Research, 2001, pp. 4245-4252, vol. 7, XP-002263075.

Miyake et al., Novel therapeutic strategy for advanced prostate cancer using antisense oligodeoxynucleotides targeting antiapoptotic genes upregulated after androgen withdrawal to delay androgen-independent progression and enhance chemosensitivity, International Journal of Urology, 2001, pp. 337-349, vol. 8, XP-002262321.

Sensibar et al., Prevention of Cell Death Induced by Tumor Necrosis Factor a in LNCaP Cells by Overexpression of Sulfated Glycoprotein-2 (Clusterin), Cancer Research, 1995, pp. 2431-2437, vol. 55, XP-002930082.

Rosenberg et al., Clusterin: Physiologic and Pathophysiologic Considerations, Int. J. Biochem. Cell Biol., 1995, pp. 633-645, vol. 27, No. 7, XP-001002844.

Wilson et al., Clusterin is a secreted mammalian chaperone, TIBS, 2000, pp. 95-97, vol. 25.

Wong et al., Molecular characterization of human TRPM-2/ clusterin, a gene associated with sperm maturation, apoptosis and neurodegeneration, Eur. J. Biochem, 1994, pp. 917-925, vol. 91, XP-001146404.

Zangemeister-Wittke et al., A Novel Bispecific Antisense Oligonucleotide Inhibiting Both bcl-2 and bcl-xL Expression Efficiently Induces Apoptosis in Tumor Cells, Clinical Cancer Research, 2000, pp. 2547-2555, Volumbe 6, XP-002241562.

Zellweger et al., Antitumor Activity of Antisense Clusterin Oligonucleotides is Improved in Vitro and in Vivo by Incorporation of 2'O'(2-Methoxy)Ethyl Chemistry, The Journal of Pharmacology and Experimental Therapeutics, 2001, pp. 934-940, vol. 298, No. 3, XP-002262318.

Zellweger et al., Chemosensitization of Human Renal Cell Cancer Using Antisense Oligonucleotides Targeting the Antiapoptotic Gene Clusterin, Neoplasia, 2001, pp. 360-367, XP-009004604.

Agrawal et al., Antisense Therapeutics: is it as simple as complementary base recognition, Molecular Medicine Today, 2000, pp. 72-81, vol. 6, Publisher: Elsevier Science Ltd.

Aoki et al., RNA Intereference may be more potent than antisense RNA in human cancer cell lines, Clinical and Experimental Pharmacology and Physiology, 2003, pp. 96-102.

Benner et al., Combination of Antisense Oligonucleotide and Low-Dose Chemotherapy in Hematological Malignancies, Journal of Pharmacological and Toxicological Methods, 1997, pp. 229-235, Publisher: Elsevier Science Inc.

Boral et al., Clinical evaluation of biologically targeted drugs: obstacles and opportunities, Cancer Chemother Pharmacol, 1998, pp. S3-S21, Publisher: Springer-Verlag.

Andrea D. Branch, A good antisense molecule is hard to find, TIBS, 1998, pp. 45-50, Publisher: Elsevier Science Ltd.

Steven Brem, MD, Angiogenesis and Cancer Control: From Concept to Therapeutic Trial, Cancer Control Journal, 1999, vol. 6, No. 5, Publisher: H. Lee Moffitt Cancer Center & Research Institute.

Bruchovsky et al., Control of Tumor Progression by Maintenance of Apoptosis, www.prostatepointers.org, 1996, Publisher: Wiley-Liss, Inc.

Buttyan et al., Induction of the TRPM-2 Gene in Cells Undergoing Programmed Death, Molecular and Cellular Biology, 1989, pp. 3473-3481, vol. 9, No. 8, Publisher: American Society for Microbiology.

Cox et al., Angiogenesis and non-small cell lung cancer, Lung Cancer, 2000, pp. 81-100, Publisher: Elsevier.

Crooke et al., Basic principles of antisense therapeutics, Antisense Research and Application, 2004, pp. 1-50, Chapter 1, Publisher: Springer.

Darby et al., Vascular Expression of Clusterin in Experimental Cyclosporine Nephrotoxicity, Exp Nephrol, 1995, pp. 234-239, Publisher: S. Karger AG.

Diemer et al., Expression of Porcine Complement Cytolysis Inhibitor mRNA in Cultured Aortic Smooth Muscle Cells, The Journal of Biological Chemistry, Mar. 15, 1992, pp. 5257-5264, vol. 207, No. 8, Publisher: The AMerican Society for Biochemistry and Molecular Biology, Inc.

Genta, New Data Realfirm Genta's Molecular Target as Critical Factor for Enhancing Anticancer Treatment, www.genta.com, 2001.

Jen et al., Suppression of Gene Expression by Targeted Disruption of Messenger RNA: Available Options and Current Strategies, Stem Cells 2000, 2000, pp. 307-319, vol. 18.

Kadomatsu et al., Expression of sulfated glycoprotein 2 is associated with carcinogenesis induced by N-nitroso-N-methylurea in rat prostate . . . , Cancer Res, Apr. 1, 1993, pp. 1480-1483, vol. 53, No. 7, abstract only.

Kirby et al, Bartonella-associated endothelial proliferation depends on inhibition of apoptosis, PNAS, Apr. 2, 2002, pp. 4656-4661, vol. 99, No. 7.

Kyprianou et al., bcl-2 over-expression delays radiation-induced apoptosis without affecting the clonogenic survival of human prostate , International Journal of Cancer, Jan. 27, 1997, pp. 341-348, vol. 70, No. 3, abstract only.

Lee et al., In Vitro Models of Prostate Apoptosis: Clusterin as an Antiapoptotic Mediator, The Prostate Supplement, 2000, pp. 21-24, vol. 9, Publisher: Wiley-Liss, Inc.

Millar et al., Localization of mRNAs by in-situ hybridization to the residual body at stages IX-X of the cycle of the rat seminiferous, International Journal of Andrology, 1994, pp. 149-160, vol. 17.

Millis et al., Clusterin Regulates Vascular Smooth Muscle Cell Nodule Formation and Migration, Journal of Cellular Physiology, 2001, pp. 210-219, vol. 186, Publisher: Wiley-Liss, Inc.

Milner et al., Selecting effective antisense reagents on combinatorial oligonucleotide arrays, Nature Biotechnology, 1997, pp. 537-541, vol. 15.

Nör et al., Engineering and Characterization of Functional Human Microvessels in Immunodeficient Mice, Laboratory Investigation, 2001, pp. 453-463, vol. 81, No. 4.

Nör et al., Up-Regulation of Bcl-2 in Microvascular Endothelial Cells Enhances Intratumoral Angiogenesis and Accelerates Tumor Growth, Mar. 1, 2001, pp. 2183-2188, vol. 61.

Opalinska et al., Nucleic-acid therapeutics: Basic principles and recent applications, Nature Reviews, 2002, pp. 503-514, vol. 1.

Tran et al., A role for survivin in chemoresistance of endothelial cells mediated by VEGF, PNAS, Apr. 2, 2002, pp. 4349-4354, vol. 99, No. 7.

Trougakos et al., Silencing Expression of the Clusterin/ Apolipoprotein J Gene in Human Cancer Cells Using Small Interfering RNA Induces, Cancer Research, Mar. 1, 2004, pp. 1834-1842, vol. 64.

Vickers et al., Efficient Reduction of Target RNAs by Small Interfering RNA and RNase H-dependent Antisense Agents, The Journal of Biological Chemistry, Feb. 28, 2003, pp. 7103-7118, vol. 278, No. 9.

Wright et al., A ribonucleotide reductase inhibitor, MDL 101,731, induces apoptosis and elevates TRPM-2 mRNA levels in human prostate , Experimental Cell Research, Jan. 10, 1996, pp. 54-60, vol. 222, No. 1, abstract only.

Yang et al., Nuclear clusterin/XIP8, an x-ray-induced Ku70-binding protein that signals cell death, PNAS, May 23, 2000, pp. 5907-5912, vol. 97, No. 11.

Zwain et al., Clusterin Protects Granulosa Cells from Apoptotic Cell Death during Follicular Atresia, Experimental Cell Research, 2000, pp. 101-110, vol. 257, Publisher: Academic Press.

\* cited by examiner

TREATMENT OF MELANOMA BY REDUCTION IN CLUSTERIN LEVELS

This application claims the benefit and priority of U.S. Provisional Applications Nos. 60/405,193 filed Aug. 21, 2002, 60/408,152 filed Sep. 3, 2002, 60/319,748 filed Dec. 2, 2002, and 60/472,387, filed May 20, 2003 all of which are incorporated herein by reference.

BACKGROUND OF THE INVENTION

This application relates to antisense treatments for melanoma by inhibition of clusterin, also known as testosterone-repressed prostate message-2 (TRPM-2), for example by the administration of antisense oligonucleotides specific for clusterin.

Clusterin or TRPM-2 is a ubiquitous protein, with a diverse range of proposed activities. In prostate epithelial cells, expression of Clusterin increases immediately following castration, reaching peak levels in rat prostate cells at 3 to 4 days post castration, coincident with the onset of massive cell death. These results have led some researchers to the conclusion that clusterin is a marker for cell death, and a promoter of apoptosis. On the other hand, the observation that Sertoli cells and some epithelial cells express high levels of clusterin without increased levels of cell death, raises questions as to whether this conclusion is correct. Sensibar et al., *Cancer Research* 55: 2431-2437 (1995) reported on in vitro experiments performed to more clearly elucidate the role of clusterin in prostatic cell death. They utilized LNCaP cells transfected with a gene encoding clusterin and observed whether expression of this protein altered the effects of tumor necrosis factor α (TNFα), to which LNCaP cells are very sensitive, with cell death normally occurring within about 12 hours. Treatment of the transfected LNCaP cells with TNFα was shown to result in a transient increase in clusterin levels for a period of a few hours, but these levels had dissipated by the time DNA fragmentation preceding cell death was observed. Using an antisense molecule corresponding to the bases 1-21 of the clusterin sequence, but not other clusterin antisense oligonucleotides, resulted in a substantial reduction in expression of clusterin, and an increase in apoptotic cell death in LNCaP cells exposed to TNFα. This led Sensibar et al. to the hypothesis that overexpression of clusterin could protect cells from the cytotoxic effect of TNF, and that clusterin depletion is responsible for the onset of cell death, although the mechanism of action remains unclear.

PCT Publication WO00/049937, which is incorporated herein by reference in all jurisdictions permitting such incorporation, describes the use of antisense therapy which reduces the expression of clusterin to provide therapeutic benefits in the treatment of cancer of prostate cancer, renal cell cancer and some breast cancers. Furthermore, combined use of antisense clusterin plus cytotoxic chemotherapy (e.g. taxanes) synergistically enhances chemosensitivity in hormone refractory prostate cancer. Radiation sensitivity is also enhanced when cells expressing clusterin are treated with antisense clusterin oligodeoxynucleotides (ODN).

SUMMARY OF THE INVENTION

The present application relates to the treatment of melanoma through reduction in the effective amount of clusterin. Thus, in accordance with one aspect of the invention, there is provided a method for treatment of melanoma in a mammalian subject, preferably a human, comprising the step of administering to the subject a therapeutic agent effective to reduce the effective amount of clusterin in the melanoma cells. The therapeutic agent may be, for example, an antisense ODN or small inhibitory RNA (siRNA) compound targeted to clusterin.

The present invention also provides a method for regulating expression of bcl-xL in a subject or cell line comprising administering to the subject or cell line an agent effective to modulate the amount of clusterin expression. In particular, in clusterin expressing cells, the expression of bcl-xL is down-regulated when the effective amount of clusterin is reduced. Such inhibition is significant because bcl-xL is known to act as an inhibitor of apoptosis. See for example U.S. Pat. No. 6,172,216 which is incorporated herein by reference.

DESCRIPTION OF THE INVENTION

As used in the specification and claims of this application, the term "clusterin" refers to the glycoprotein originally derived from rat testes, and to homologous proteins derived from other mammalian species, including humans, whether denominated as clusterin or an alternative name. The sequences of numerous clusterin species are known. For example, the sequence of human clusterin is reported by Wong et al., *Eur. J. Biochem.* 221 (3), 917-925 (1994), and in NCBI sequence accession number NM_001831 and is set forth in the Sequence Listing as Seq. ID. No. 1. In this sequence, the coding sequence spans bases 48 to 1397.

The present invention provides a therapeutic composition, and methods for using such a composition for treatment of melanoma, particularly in humans. The therapeutic compositions and methods of the invention achieve a reduction in the effective amount of clusterin present in the individual being treated. As used in this application, the "effective amount of clusterin" is the amount of clusterin which is present in a form which is functional to provide anti-apoptotic protection. The effective amount of clusterin may be reduced by decreasing the expression rate of clusterin, increasing the rate of clusterin degradation, or by modifying clusterin (for example by binding with an antibody) such that it is rendered inactive.

Antisense ODN Therapeutics

In one embodiment of the invention, reduction in the effective amount of clusterin may be accomplished by the administration of antisense ODNs, particularly antisense ODNs which are complementary to a region of the clusterin mRNA spanning either the translation initiation site or the termination site. Exemplary sequences which can be employed as antisense molecules in the method of the invention are disclosed in PCT Patent Publication WO 00/49937, US Patent Publication US-2002-0128220-A1, and U.S. Pat. No. 6,383,808, all of which are incorporated herein by reference in those jurisdictions where such incorporation is permitted. Specific antisense sequences are set forth in the present application as Seq. ID Nos.: 2 to 12.

The ODNs employed may be modified to increase the stability of the ODN in vivo. For example, the ODNs may be employed as phosphorothioate derivatives (replacement of a non-bridging phosphoryl oxygen atoms with a sulfur atom) which have increased resistance to nuclease digestion. MOE (2'-O-(2-methoxyethyl) modification (ISIS backbone) is also effective. Construction of such modified ODN is described in detail in U.S. patent application Ser. No. 10/080,794 which is incorporated herein by reference in those jurisdictions permitting such incorporation. A particularly preferred composition is a 21mer oligonucleotide (cagcagcagagtcttcatcat; SEQ ID NO: 4) targeted to the translation initiation codon and next 6 codons of the human clusterin sequence (Genbank accession no: NM_001831) with a 2'-MOE modification. This oligonucleotide has a phosphorothioate backbone throughout. The sugar moieties of nucleotides 1-4 and 18-21 (the "wings") bear 2'-O-methoxyethyl modifications and the remaining nucleotides (nucleotides 5-17; the "deoxy gap") are 2'-deoxynucleotides. Cytosines in the wings (i.e., nucleotides 1, 4 and 19) are 5-methylcytosines.

Administration of antisense ODNs can be carried out using the various mechanisms known in the art, including naked administration and administration in pharmaceutically acceptable lipid carriers. For example, lipid carriers for antisense delivery are disclosed in U.S. Pat. Nos. 5,855,911 and 5,417,978 which are incorporated herein by reference. In general, the antisense is administered by intravenous, intraperitoneal, subcutaneous or oral routes, or direct local tumor injection.

The amount of antisense ODN administered is one effective to inhibit the expression of Clusterin in melanoma cells. It will be appreciated that this amount will vary both with the effectiveness of the antisense ODN employed, and with the nature of any carrier used. The determination of appropriate amounts for any given composition is within the skill in the art, through standard series of tests designed to assess appropriate therapeutic levels.

RNAi Therapeutics

Reduction in the effective amount of clusterin can also be achieved using RNAi therapy. RNA interference or "RNAi" is a term initially coined by Fire and co-workers to describe the observation that double-stranded RNA (dsRNA) can block gene expression when it is introduced into worms (Fire et al. (1998) Nature 391, 806-811, incorporated herein by reference). dsRNA directs gene-specific, post-transcriptional silencing in many organisms, including vertebrates, and has provided a new tool for studying gene function. RNAi involves mRNA degradation, but many of the biochemical mechanisms underlying this interference are unknown. The use of RNAi has been further described in Carthew et al. (2001) Current Opinions in Cell Biology 13, 244-248, and Elbashir et al. (2001) Nature 411, 494-498, both of which are incorporated herein by reference.

In the present invention, isolated RNA molecules mediate RNAi. That is, the isolated RNA molecules of the present invention mediate degradation or block expression of mRNA that is the transcriptional product of the gene, which is also referred to as a target gene. For convenience, such mRNA may also be referred to herein as mRNA to be degraded. The terms RNA, RNA molecule(s), RNA segment(s) and RNA fragment(s) may be used interchangeably to refer to RNA that mediates RNA interference. These terms include double-stranded RNA, single-stranded RNA, isolated RNA (partially purified RNA, essentially pure RNA, synthetic RNA, recombinantly produced RNA), as well as altered RNA that differs from naturally occurring RNA by the addition, deletion, substitution and/or alteration of one or more nucleotides. Such alterations can include addition of non-nucleotide material, such as to the end(s) of the RNA or internally (at one or more nucleotides of the RNA). Nucleotides in the RNA molecules of the present invention can also comprise non-standard nucleotides, including non-naturally occurring nucleotides or deoxyribonucleotides. Collectively, all such altered RNAi molecules are referred to as analogs or analogs of naturally-occurring RNA. RNA of the present invention need only be sufficiently similar to natural RNA that it has the ability to mediate RNAi. As used herein the phrase "mediate RNAi" refers to and indicates the ability to distinguish which mRNA are to be affected by the RNAi machinery or process. RNA that mediates RNAi interacts with the RNAi machinery such that it directs the machinery to degrade particular mRNAs or to otherwise reduce the expression of the target protein. In one embodiment, the present invention relates to RNA molecules that direct cleavage of specific mRNA to which their sequence corresponds. It is not necessary that there be perfect correspondence of the sequences, but the correspondence must be sufficient to enable the RNA to direct RNAi inhibition by cleavage or blocking expression of the target mRNA.

As noted above, the RNA molecules of the present invention in general comprise an RNA portion and some additional portion, for example a deoxyribonucleotide portion. The total number of nucleotides in the RNA molecule is suitably less than 49 in order to be effective mediators of RNAi. In preferred RNA molecules, the number of nucleotides is 16 to 29, more preferably 18 to 23, and most preferably 21-23. Suitable sequences are set forth in the present application as Seq. ID Nos. 20 to 43.

The siRNA molecules of the invention are used in therapy to treat patients, including human patients, that have cancers or other diseases of a type where a therapeutic benefit is obtained by the inhibition of expression of the targeted protein. siRNA molecules of the invention are administered to patients by one or more daily injections (intravenous, subcutaneous or intrathecal) or by continuous intravenous or intrathecal administration for one or more treatment cycles to reach plasma and tissue concentrations suitable for the regulation of the targeted mRNA and protein.

Additional Therapeutic Agents

The method for treating melanoma in accordance with the invention may further include administration of chemotherapy agents or other agents useful in melanoma therapy and/or additional antisense ODNs directed at different targets in combination with the therapeutic effective to reduce the amount of active clusterin. For example, antisense clusterin ODN increases sensitivity to conventional chemotherapy agents as taxanes (paclitaxel or docetaxel), mitoxanthrone, and gemcitabine. Other agents likely to show synergistic activity include other cytotoxic agents (e.g. cyclophosphamide, decarbazine, topoisomerase inhibitors), angiogenesis inhibitors, differentiation agents and signal transduction inhibitors. Similarly, combinations of clusterin antisense with other antisense species such as antisense Bcl-2, Bcl-xl and c-myc ODN to provide greater effectiveness.

Method of Regulating Bcl-xL Expression

Figure 3:
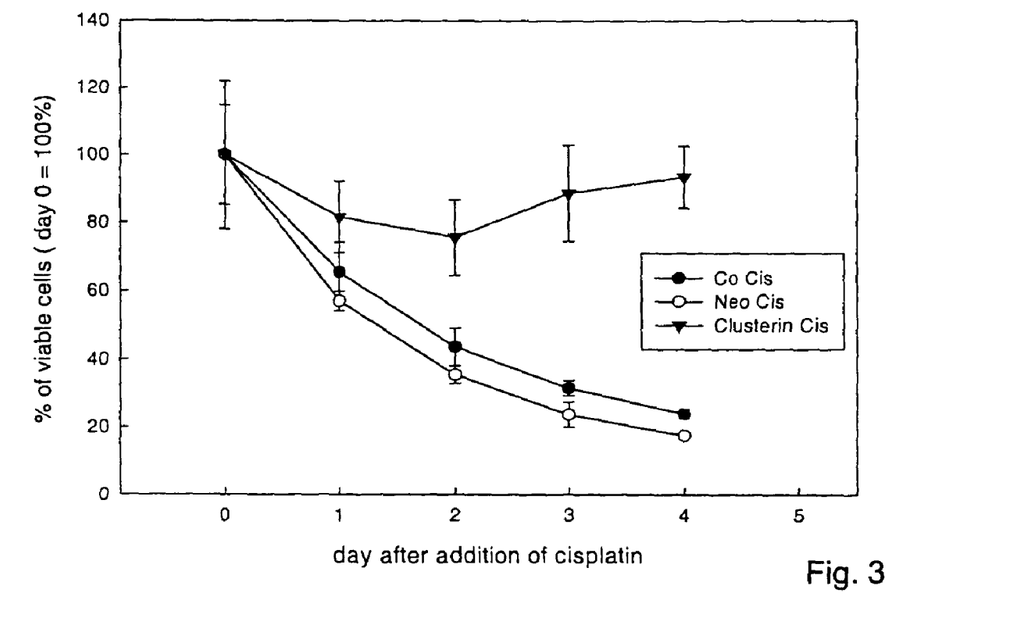
FIG. 3 shows cell survival of Mel Juso melanoma cells stably transfected with either an empty control vector (Neo) or a vector directing overexpression of clusterin were grown in medium containing 10 µM cisplatin.

While chaperone-like function has been proposed for the clusterin protein, the specific molecular mechanism responsible for clusterin's role in apoptosis remains elusive. In the human melanoma cell line that expressed clusterin at a very low levels, over-expression of clusterin by stable transfection not only led to a marked increase in resistance to a cytotoxic treatment (FIG. 3), but led also to an up-regulation of the anti-apoptotic bcl-2 family member bcl-xL as shown by Western blotting. Conversely treatment of clusterin-expressing melanoma cells led to a marked down-regulation of bcl-xL thus providing a possible mechanism for the antiapoptotic potency of clusterin. Neither clusterin overexpression by transfection nor clusterin antisense treatment altered the expression of other Bcl-2 family members tested in human melanoma cells. Thus, clusterin regulates the anti-apoptotic bcl-2 family member bcl-xL. Such inhibition is significant because bcl-xL is known to act as an inhibitor of apoptosis (See U.S. Pat. No. 6,182,216 which is incorporated herein by reference in those jurisdictions permitting such incorporation).

The invention will now be further described with reference to the following, non-limiting examples.

EXAMPLE 1

Expression of clusterin in two different batches of normal human melanocytes (NHEM 6083 and 2489) and four human melanoma cell lines (518A2, SKMEL-28, Mel-Juso and 607B). Cells were grown in 6 cm dishes and harvested when they were 80-90% confluent. 30 µg of protein per lane was applied onto a 10% SDS-Page gel and probed with a polyclonal goat anti-clusterin antibody. Panceau red stain and an antibody directed against β-actin were used as a loading control. In each case, the antisense inhibitor of clusterin used is based on the advanced antisense chemistry 2'MOE as described in U.S. patent application Ser. No. 10/080,794 and has the sequence of Seq. ID. NO. 4.

Figure 1:
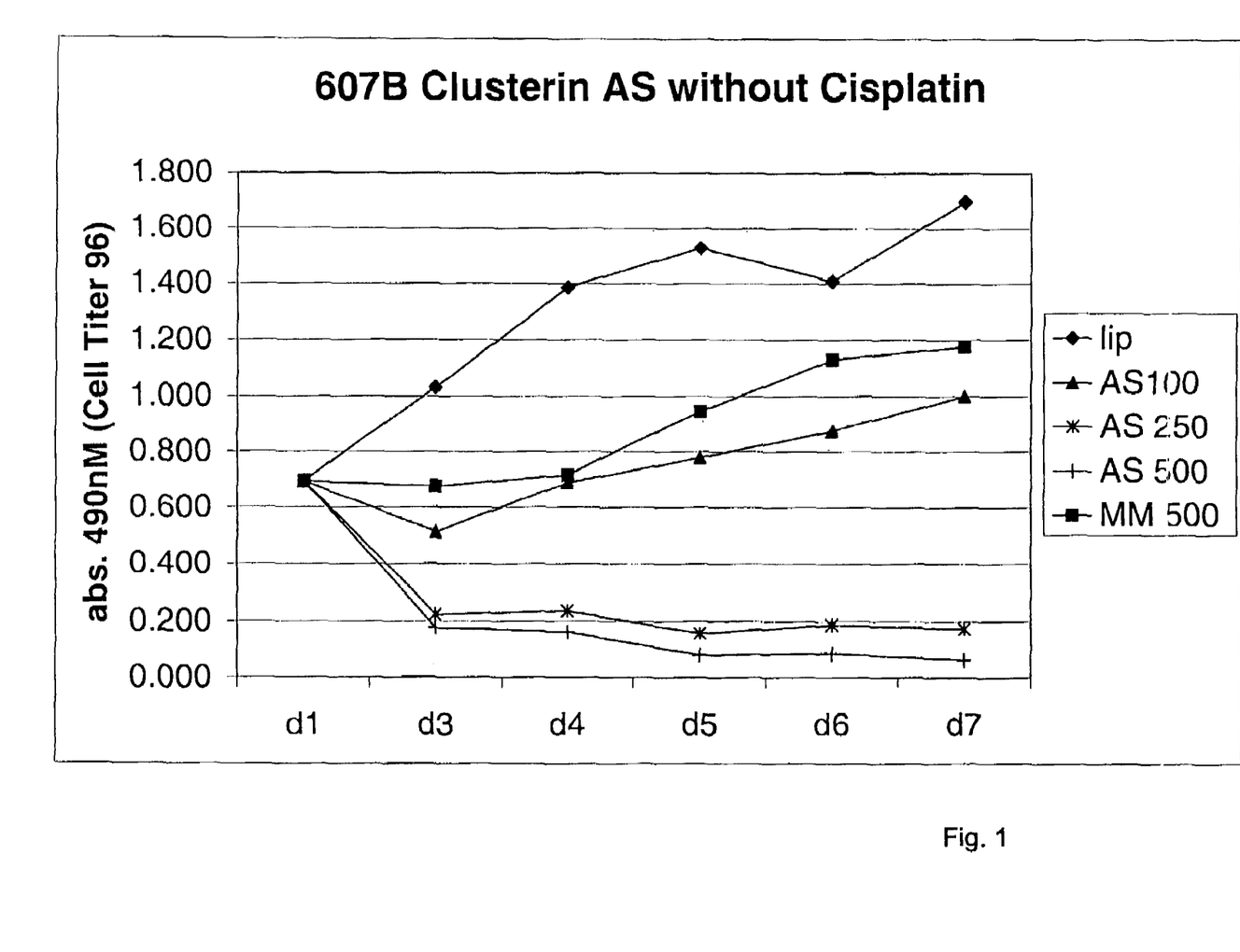
FIG. 1 shows the results when 607B melanoma cells were treated with either the antisense oligonucleotide at concentrations of 100, 250 or 500 nM, or a scrambled mismatch control at a concentration of 100 nM on two consecutive days.

FIG. 1 shows the results when 607B melanoma cells were treated with either the antisense oligonucleotide at concentrations of 100, 250 or 500 nM, or a scrambled control at a concentration of 100 nM on two consecutive days. Lipofectin™ (lip) without oligonucleotide was used as a control. Cells numbers in 96 well plates were measured photometrically using MTS (Cell Titer 96™, Pierce). As shown, cell counts in the presence of antisense treated wells at 250 and 500 nM are significantly reduced.

Figure 2:
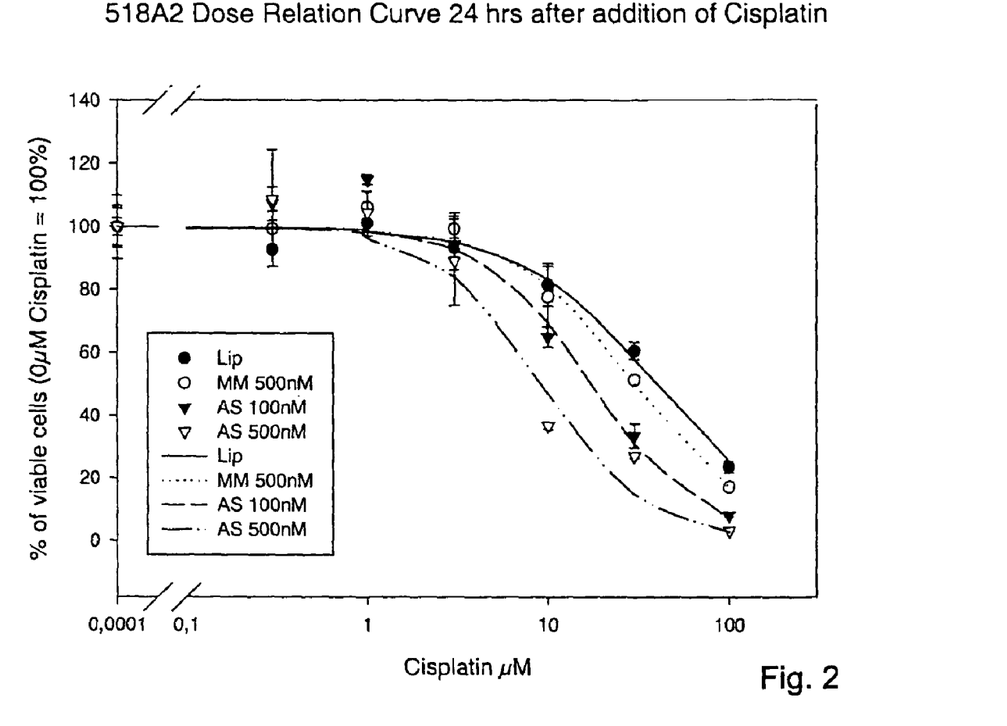
FIG. 2 provides a graphic representations of clusterin expression in 518A2 cells after treatment with cisplatin and either an antisense oligonucleotide or a scrambled, mismatch control.

FIG. 2 provides a graphic representations of clusterin expression in 518A2 cells after treatment with cisplatin and either an antisense oligonucleotide or a scrambled control. Lip is a Lipofectin control without oligonucleotide. Detection was performed using an antibody directed against clusterin.

The results in showed that in human melanoma cells clusterin is expressed at significantly higher levels than in human melanocytes in all but one cell line tested. The antisense inhibitor (MOE modification of Seq. ID. NO. 4) led to a dose dependent down-regulation of clusterin as shown by RT-PCR on the mRNA level and by western-blot on the protein level as compared to the scrambled mismatch control. This down-regulation led to an increase in apoptotic cell death by antisense treatment alone. In one melanoma cell line (607B) this alone was sufficient to lead to complete cell death. (FIG. 1) In another melanoma cell line the surviving cells showed increased sensitivity to an consecutive treatment with the cytotoxic drug cisplatin as compared to cells treated with a control-mismatch oligonucleotide (FIG. 2).

EXAMPLE 2

Mel Juso melanoma cells stably tranfected with either an empty control vector (Neo) or a vector directing overepression of clusterin were grown in medium containing 10 µM cisplatin. Cell survival was measured using the Cell-titer 96 kits from Promega. The results are summarized in FIG. 3. As shown, overexpression of clusterin dramatically enhanced cell survival, or said differently, reduced the effectiveness of the chemotherapy agent.

The invention claimed is:

1. A method for treatment of melanoma in a mammalian subject, comprising the step of administering to the subject a therapeutic agent effective to reduce the amount of clusterin in the melanoma cells, wherein the therapeutic agent is an oligonucleotide that targets clusterin and that has a sequence complementary to clusterin-encoding mRNA.

2. The method of claim 1, wherein the therapeutic agent is an antisense oligodeoxynucleotide.

3. The method of claim 2, wherein the antisense oligodeoxynucleotide spans either the translation initiation site or the termination site.

4. The method of claim 3, wherein the antisense oligodeoxynucleotide is modified to enhance in vivo stability relative to an unmodified oligodeoxynucleotide of the same sequence.

5. The method of claim 4, wherein the modification is a 2'-0-(2-methoxyethyl) modification.

6. The method of claim 5, wherein the antisense oligodeoxynucleotide consists essentially of an oligodeoxynucleotide selected from the group consisting of Seq. ID. Nos. 2 to 12.

7. The method of claim 6, wherein the antisense oligodeoxynucleotide consists essentially of an oligodeoxynucleotide consisting of Seq. ID. No. 4.

8. The method of claim 7, wherein the oligonucleotide has a phosphorothioate backbone throughout, the sugar moieties of nucleotides 1-4 and 18-21, the "wings", bear 2'-O-methoxyethyl modifications and the remaining nucleotides are 2'-deoxynucleotides.

9. The method of claim 2, wherein the antisense oligodeoxynucleotide consists essentially of an oligodeoxynucleotide selected from the group consisting of Seq. ID. Nos. 2 to 12.

10. The method of claim 9, wherein the antisense oligodeoxynucleotide consists essentially of an oligodeoxynucleotide consisting of Seq. ID. No. 4.

11. The method of claim 1 wherein the therapeutic agent is an RNA molecule effective to reduce the amount of clusterin in the melanoma cells by an RNAi mechanism.

12. The method of claim 11, wherein the RNA molecule consists essentially of an oligodeoxynucleotide selected from the group consisting of Seq. ID. Nos.20 to 25.

* * * * *

SEQUENCE LISTING

```
<160> NUMBER OF SEQ ID NOS: 43

<210> SEQ ID NO 1
<211> LENGTH: 1676
<212> TYPE: DNA
<213> ORGANISM: human

<400> SEQUENCE: 1
gaattccgcc gctgaccgag gcgtgcaaag actccagaat tggaggcatg atgaagactc      60
tgctgctgtt tgtggggctg ctgctgacct gggagagtgg gcaggtcctg ggggaccaga     120
cggtctcaga caatgagctc caggaaatgt ccaatcaggg aagtaagtac gtcaataagg     180
aaattcaaaa tgctgtcaac ggggtgaaac agataaagac tctcatagaa aaaacaaacg     240
aagagcgcaa gacactgctc agcaacctag aagaagccaa gaagaagaaa gaggatgccc     300
taaatgagac cagggaatca gagacaaagc tgaaggagct cccaggagtg tgcaatgaga     360
ccatgatggc cctctgggaa gagtgtaagc cctgcctgaa acagacctgc atgaagttct     420
acgcacgcgt ctgcagaagt ggctcaggcc tggttggccg ccagcttgag gagttcctga     480
```

-continued

```
accagagctc gcccttctac ttctggatga atggtgaccg catcgactcc ctgctggaga       540
acgaccggca gcagacgcac atgctggatg tcatgcagga ccacttcagc cgcgcgtcca       600
gcatcataga cgagctcttc caggacaggt tcttcacccg ggagcccag gatacctacc        660 actacctgcc cttcagcctg ccccaccgga ggcctcactt cttctttccc aagtcccgca       720
tcgtccgcag cttgatgccc ttctctccgt acgagcccct gaacttccac gccatgttcc       780
agcccttcct tgagatgata cacgaggctc agcaggccat ggacatccac ttccacagcc       840
cggccttcca gcacccgcca acagaattca tacgagaagg cgacgatgac cggactgtgt       900
gccgggagat ccgccacaac tccacgggct gcctgcggat gaaggaccag tgtgacaagt       960
gccgggagat cttgtctgtg gactgttcca ccaacaaccc ctcccaggct aagctgcggc      1020
gggagctcga cgaatccctc caggtcgctg agaggttgac caggaaatac aacgagctgc      1080
taaagtccta ccagtggaag atgctcaaca cctcctcctt gctggagcag ctgaacgagc      1140
agtttaactg ggtgtcccgg ctgcaaaacc tcacgcaagg cgaagaccag tactatctgc      1200
gggtcaccac ggtggcttcc cacacttctg actcggacgt tccttccggt gtcactgagg      1260
tggtcgtgaa gctctttgac tctgatccca tcactgtgac ggtccctgta gaagtctcca      1320
ggaagaaccc taaatttatg gagaccgtgg cggagaaagc gctgcaggaa taccgcaaaa      1380
agcaccggga ggagtgagat gtggatgttg cttttgcacc ttacggggc atcttgagtc       1440 cagctccccc caagatgagc tgcagccccc cagagagagc tctgcacgtc accaagtaac      1500
caggccccag cctccaggcc cccaactccg cccagcctct ccccgctctg gatcctgcac      1560
tctaacactc gactctgctg ctcatgggaa gaacagaatt gctcctgcat gcaactaatt      1620
caataaaact gtcttgtgag ctgaaaaaaa aaaaaaaaaa aaaaaaaaag gaattc          1676
```

<210> SEQ ID NO 2
<211> LENGTH: 21
<212> TYPE: DNA
<213> ORGANISM: murine

<400> SEQUENCE: 2
gcacagcagg agaatcttca t                                                 21

<210> SEQ ID NO 3
<211> LENGTH: 21
<212> TYPE: DNA
<213> ORGANISM: human

<400> SEQUENCE: 3
tggagtcttt gcacgcctcg g                                                 21

<210> SEQ ID NO 4
<211> LENGTH: 21
<212> TYPE: DNA
<213> ORGANISM: human

<400> SEQUENCE: 4
cagcagcaga gtcttcatca t                                                 21

<210> SEQ ID NO 5
<211> LENGTH: 21
<212> TYPE: DNA
<213> ORGANISM: human

<400> SEQUENCE: 5
attgtctgag accgtctggt c                                                 21

```
<210> SEQ ID NO 6
<211> LENGTH: 21
<212> TYPE: DNA
<213> ORGANISM: human

<400> SEQUENCE: 6
ccttcagctt tgtctctgat t                                             21

<210> SEQ ID NO 7
<211> LENGTH: 21
<212> TYPE: DNA
<213> ORGANISM: human

<400> SEQUENCE: 7
agcagggagt cgatgcggtc a                                             21

<210> SEQ ID NO 8
<211> LENGTH: 21
<212> TYPE: DNA
<213> ORGANISM: human

<400> SEQUENCE: 8
atcaagctgc ggacgatgcg g                                             21

<210> SEQ ID NO 9
<211> LENGTH: 21
<212> TYPE: DNA
<213> ORGANISM: human

<400> SEQUENCE: 9
gcaggcagcc cgtggagttg t                                             21

<210> SEQ ID NO 10
<211> LENGTH: 21
<212> TYPE: DNA
<213> ORGANISM: human

<400> SEQUENCE: 10
ttcagctgct ccagcaagga g                                             21

<210> SEQ ID NO 11
<211> LENGTH: 21
<212> TYPE: DNA
<213> ORGANISM: human

<400> SEQUENCE: 11
aatttagggt tcttcctgga g                                             21

<210> SEQ ID NO 12
<211> LENGTH: 21
<212> TYPE: DNA
<213> ORGANISM: human

<400> SEQUENCE: 12
gctgggcgga gttggggggcc t                                            21

<210> SEQ ID NO 13
<211> LENGTH: 17
<212> TYPE: DNA
<213> ORGANISM: human

<400> SEQUENCE: 13
```

```
ggtgtagacg ccgcacg                                                    17

<210> SEQ ID NO 14
<211> LENGTH: 16
<212> TYPE: DNA
<213> ORGANISM: human

<400> SEQUENCE: 14
gcagcgcagc ccctgg                                                     16

<210> SEQ ID NO 15
<211> LENGTH: 22
<212> TYPE: DNA
<213> ORGANISM: human

<400> SEQUENCE: 15
gcagcagccg cagcccggct cc                                              22

<210> SEQ ID NO 16
<211> LENGTH: 18
<212> TYPE: DNA
<213> ORGANISM: human

<400> SEQUENCE: 16
agccgcagcc cggctcct                                                   18

<210> SEQ ID NO 17
<211> LENGTH: 20
<212> TYPE: DNA
<213> ORGANISM: human

<400> SEQUENCE: 17
cagcagccgc agcccggctc                                                 20

<210> SEQ ID NO 18
<211> LENGTH: 20
<212> TYPE: DNA
<213> ORGANISM: human

<400> SEQUENCE: 18
gcagcagccg cagcccggct                                                 20

<210> SEQ ID NO 19
<211> LENGTH: 20
<212> TYPE: DNA
<213> ORGANISM: human

<400> SEQUENCE: 19
agcagccgca gcccggctcc                                                 20

<210> SEQ ID NO 20
<211> LENGTH: 21
<212> TYPE: DNA
<213> ORGANISM: artificial
<220> FEATURE:
<223> OTHER INFORMATION: RNAi for human clusterin

<400> SEQUENCE: 20
ccagagcucg cccuucuact t                                               21

<210> SEQ ID NO 21
<211> LENGTH: 21
<212> TYPE: DNA
<213> ORGANISM: artificial
```

```
<220> FEATURE:
<223> OTHER INFORMATION: RNAi for human clusterin

<400> SEQUENCE: 21
guagaagggc gagcucuggt t                                              21

<210> SEQ ID NO 22
<211> LENGTH: 21
<212> TYPE: DNA
<213> ORGANISM: artificial
<220> FEATURE:
<223> OTHER INFORMATION: RNAi for human clusterin

<400> SEQUENCE: 22
gaugcucaac accuccucct t                                              21

<210> SEQ ID NO 23
<211> LENGTH: 21
<212> TYPE: DNA
<213> ORGANISM: artificial
<220> FEATURE:
<223> OTHER INFORMATION: RNAi for human clusterin

<400> SEQUENCE: 23
ggaggaggug uugagcauct t                                              21

<210> SEQ ID NO 24
<211> LENGTH: 19
<212> TYPE: DNA
<213> ORGANISM: artificial
<220> FEATURE:
<223> OTHER INFORMATION: RNAi for human clusterin

<400> SEQUENCE: 24
uaauucaaca aaacugutt                                                 19

<210> SEQ ID NO 25
<211> LENGTH: 21
<212> TYPE: DNA
<213> ORGANISM: artificial
<220> FEATURE:
<223> OTHER INFORMATION: RNAi for human clusterin

<400> SEQUENCE: 25
gacaguuuua uugaauuagt t                                              21

<210> SEQ ID NO 26
<211> LENGTH: 19
<212> TYPE: DNA
<213> ORGANISM: artificial
<220> FEATURE:
<223> OTHER INFORMATION: RNAi for human clusterin

<400> SEQUENCE: 26
uaauucaaca aaacugutt                                                 19

<210> SEQ ID NO 27
<211> LENGTH: 19
<212> TYPE: DNA
<213> ORGANISM: artificial
<220> FEATURE:
<223> OTHER INFORMATION: RNAi for human clusterin

<400> SEQUENCE: 27
acaguuuugu ugaauuatt                                                 19
```

```
<210> SEQ ID NO 28
<211> LENGTH: 21
<212> TYPE: DNA
<213> ORGANISM: artificial
<220> FEATURE:
<223> OTHER INFORMATION: RNAi for human clusterin

<400> SEQUENCE: 28
augaugaaga cucugcugct t                                              21

<210> SEQ ID NO 29
<211> LENGTH: 21
<212> TYPE: DNA
<213> ORGANISM: artificial
<220> FEATURE:
<223> OTHER INFORMATION: RNAi for human clusterin

<400> SEQUENCE: 29
gcagcagagu cuucaucaut t                                              21

<210> SEQ ID NO 30
<211> LENGTH: 22
<212> TYPE: DNA
<213> ORGANISM: artificial
<220> FEATURE:
<223> OTHER INFORMATION: RNAi for human clusterin

<400> SEQUENCE: 30
ugaaugaagg gacuaaccug tt                                             22

<210> SEQ ID NO 31
<211> LENGTH: 22
<212> TYPE: DNA
<213> ORGANISM: artificial
<220> FEATURE:
<223> OTHER INFORMATION: RNAi for human clusterin

<400> SEQUENCE: 31
cagguuaguc ccuucauuca tt                                             22

<210> SEQ ID NO 32
<211> LENGTH: 22
<212> TYPE: DNA
<213> ORGANISM: artificial
<220> FEATURE:
<223> OTHER INFORMATION: RNAi for human clusterin

<400> SEQUENCE: 32
cagaaauaga caaagugggg tt                                             22

<210> SEQ ID NO 33
<211> LENGTH: 22
<212> TYPE: DNA
<213> ORGANISM: artificial
<220> FEATURE:
<223> OTHER INFORMATION: RNAi for human clusterin

<400> SEQUENCE: 33
ccccacuuug ucuauuucug tt                                             22

<210> SEQ ID NO 34
<211> LENGTH: 22
<212> TYPE: DNA
<213> ORGANISM: artificial
<220> FEATURE:
<223> OTHER INFORMATION: RNAi for human clusterin
```

<400> SEQUENCE: 34
acagagacua agggaccaga tt						22

<210> SEQ ID NO 35
<211> LENGTH: 22
<212> TYPE: DNA
<213> ORGANISM: artificial
<220> FEATURE:
<223> OTHER INFORMATION: RNAi for human clusterin

<400> SEQUENCE: 35
acagagacua agggaccaga tt						22

<210> SEQ ID NO 36
<211> LENGTH: 21
<212> TYPE: DNA
<213> ORGANISM: artificial
<220> FEATURE:
<223> OTHER INFORMATION: RNAi for human clusterin

<400> SEQUENCE: 36
ccagagcucg cccuucuact t						21

<210> SEQ ID NO 37
<211> LENGTH: 21
<212> TYPE: DNA
<213> ORGANISM: artificial
<220> FEATURE:
<223> OTHER INFORMATION: RNAi for human clusterin

<400> SEQUENCE: 37
guagaagggc gagcucuggt t						21

<210> SEQ ID NO 38
<211> LENGTH: 21
<212> TYPE: DNA
<213> ORGANISM: artificial
<220> FEATURE:
<223> OTHER INFORMATION: RNAi for human clusterin

<400> SEQUENCE: 38
gucccgcauc guccgcagct t						21

<210> SEQ ID NO 39
<211> LENGTH: 21
<212> TYPE: DNA
<213> ORGANISM: artificial
<220> FEATURE:
<223> OTHER INFORMATION: RNAi for human clusterin

<400> SEQUENCE: 39
gcugcggacg augcgggact t						21

<210> SEQ ID NO 40
<211> LENGTH: 21
<212> TYPE: DNA
<213> ORGANISM: artificial
<220> FEATURE:
<223> OTHER INFORMATION: RNAi for human clusterin

<400> SEQUENCE: 40
cuaauucaau aaaacuguct t						21

<210> SEQ ID NO 41

```
<211> LENGTH: 21
<212> TYPE: DNA
<213> ORGANISM: artificial
<220> FEATURE:
<223> OTHER INFORMATION: RNAi forhuman clusterin

<400> SEQUENCE: 41
gacaguuuua uugaauuagt t                                              21

<210> SEQ ID NO 42
<211> LENGTH: 19
<212> TYPE: RNA
<213> ORGANISM: artificial
<220> FEATURE:
<223> OTHER INFORMATION: RNAi for human clusterin

<400> SEQUENCE: 42
augaugaaga cucugcugc                                                 19

<210> SEQ ID NO 43
<211> LENGTH: 19
<212> TYPE: RNA
<213> ORGANISM: artificial
<220> FEATURE:
<223> OTHER INFORMATION: RNAi fo rhuman clusterin

<400> SEQUENCE: 43
gcagcagagu cuucaucau                                                 19
```